United States Patent [19]

Yokota et al.

[11] Patent Number: 5,318,788
[45] Date of Patent: Jun. 7, 1994

[54] METHOD FOR IMPROVING PIGMENTATION OF RIND OF APPLE

[75] Inventors: Kiyoshi Yokota, Iwate; Tohru Tanaka; Yasushi Hotta, both of Saitama, all of Japan

[73] Assignee: Cosmo Research Institute, Tokyo, Japan

[21] Appl. No.: 151,264

[22] Filed: Nov. 12, 1993

[30] Foreign Application Priority Data

Nov. 12, 1992 [JP] Japan .................................. 4-302590

[51] Int. Cl.⁵ ............................................. A23L 1/272
[52] U.S. Cl. ..................................... 426/268; 426/102; 426/250; 426/262; 426/656; 47/58
[58] Field of Search ............... 426/262, 250, 268, 102, 426/656; 47/58

*Primary Examiner*—Helen Pratt
*Attorney, Agent, or Firm*—Sughrue, Mion, Zinn, Macpeak & Seas

[57] ABSTRACT

A method for improving pigmentation of the rind of anthocyanin-containing apples comprising treating fruit-bearing apple trees or apples before or after harvesting with an effective amount of an agent which comprises 5-aminolevulinic acid, a salt thereof or a mixture thereof as an active component.

4 Claims, No Drawings

METHOD FOR IMPROVING PIGMENTATION OF RIND OF APPLE

FIELD OF THE INVENTION

This invention relates to a method for improving the red pigmentation of the rind of anthocyanin-containing apples.

BACKGROUND OF THE INVENTION

The degree of pigmentation of the rind of apples is one of the very important quality requirements and it determines their market value. Improvement in the degree of pigmentation of apple rind has been an important subject for apple growers.

While the mechanism of action in pigmentation of apple rind has not yet been elucidated completely, it is known that sufficient exposure to sunlight leads to an improvement in pigmentation. In order to provide more sunlight, a practice widely followed is to lay a silvery sheet under the trees or to thin out the foliage. However, these methods of increasing the amount of sunlight exposure not only cost the growers a large amount of labor but produce insufficient effects. In addition, thinning the foliage decreases the vigor of the plant.

On the other hand, an approach for improving pigmentation of apple rind by using a chemical agent has also been made. However, a number of chemically synthesized agricultural chemicals, including agents for improving pigmentation of apples, have been revealed to have high toxicity or to remain and accumulate in the environment. For example, recently a permission to "Alar" (SADH) developed for that purpose was revoked on suspicion of carcinogenicity. Therefore, development of naturally occurring substances which have low toxicity and do not remain in the environment has attracted attention as a new direction to be taken in agricultural chemistry.

SUMMARY OF THE INVENTION

An object of the present invention is to provide a method for improving the pigmentation of the rind of anthocyanin-containing apples which is safe, the using agent does not remain in the environment, and produces excellent effects.

For the purpose of finding a component improving pigmentation of the rind of apples from naturally occurring substances, extensive investigations have been conducted and it has been found, as a result, that 5-aminolevulinic acid (hereinafter abbreviated as 5-ALA) known as a natural amino acid or a salt thereof or a mixture thereof has the effect of improving pigmentation of apple rind. The present invention has been completed based on this finding.

The present invention provides a method for improving the pigmentation of the rind of anthocyanin-containing apples comprising treating fruit-bearing apple trees or apples before or after harvesting with an agent for improving the pigmentation of the rind of apples (hereinafter simply referred to as a pigmentation improving agent) comprising 5-ALA, a salt thereof or a mixture thereof as an active component.

DETAILED DESCRIPTION OF THE INVENTION

5-ALA or its salt which can be used in the present invention can be prepared by chemical synthesis, microbiological production or enzymatic production. The technique disclosed in JP-A-2-92293 (the term "JP-A" as used herein means an "unexamined published Japanese patent application") is an example of a microbiological production method. Where a microbiological or enzymatic technique is followed, the product may be used as it is without isolation and purification unless it contains a substance harmful to apples or the environment.

Salts of 5-ALA which can be used in the present invention include acid addition salts, e.g., a hydrochloride, a phosphate, a nitrate, a sulfate, an acetate, a propionate, a butyrate, a valerate, a citrate, a fumarate, a maleate, and a malate; and metal salts, e.g., a sodium salt, a potassium salt, and a calcium salt.

These 5-ALA salts are dissolved in water on use and are equal to 5-ALA in effect. 5-ALA and salts thereof may be used either individually or as a combination of two or more thereof.

5-ALA and salts thereof are substances of extremely low toxicity which broadly occur in nature and also exist in the human body. Further, they are easily degraded in nature by the action of microorganisms and the like and hardly remain in the environment.

The pigmentation improving agent used in the present invention may consist solely of 5-ALA, a salt thereof or a mixture thereof or it may, if desired, further contain other chemicals or additives, such as spreading agents, saccharides, amino acids, organic acids, alcohols, vitamins, minerals, and so forth. Specific examples of useful spreading agents include polyoxyethylene fatty acid esters (e.g., polyoxyethylenehexitan fatty acid ester), polyoxyethylene resin acid esters, polyoxyethylene alkylphenyl ethers (e.g., polyoxyethylene nonylphenyl ether), and mixtures thereof.

The pigmentation improving agent used in the present invention may be formulated into powders, granules, solutions, etc. in a usual manner by using solvents, dispersing media, thickeners, etc.

The method for improving pigmentation of apple rind according to the present invention comprises treating fruit-bearing apple trees or apples before or after harvesting with the above-mentioned pigmentation improving agent. The manner of treatment is not particularly restricted as long as the pigmentation improving agent adheres to the whole or branches of an apple tree or apple fruit. For example, the treatment can be carried out by spraying a solution containing the pigmentation improving agent or dipping apples in the solution.

In a case of treating, for example, about 20 grown apple trees per 1000 m$^2$ (an example of a usual orchard) with 5-ALA, the amount of 5-ALA is from about 10 to 4000 liter, preferably from about 100 to 1000 liter per 1000 m$^2$.

The pigmentation improving agent is used in a concentration of from 1 to 1000 ppm, and preferably from 3 to 800 ppm, in terms of 5-ALA. 5-ALA concentrations less than 1 ppm tend to fail to show sufficient effects. 5-ALA concentrations exceeding 1000 ppm, when applied before harvesting, tend to cause leaf scorch.

The treatment with the pigmentation improving agent is usually performed once for obtaining sufficient effects or, if desired, may be conducted two or more times for obtaining greater effects.

The kinds of apples to which the pigmentation improvement according to the present invention is applicable are not particularly limited as long as the rind thereof has a red color, i.e., anthocyanin pigments. Specific but non-limiting apple varieties are Delicious, Starking Delicious, Akane, Fuji, Tsugaru, Mutsu, Kokko, Jonathan, Hokuto, Shinsekai, Hakkunain, Jonagold, Redgold, Sensyu, McIntosh, Sansa, Rome Beauty, Winesap, Gala, etc. Green apples which do not have any red pigments (those apples whose rind has a green color even when ripen) do not turn red even if treated according to the present invention.

The method for improving pigmentation of apple rind according to the present invention chiefly acts on improving the pigmentation of apple rind without adversely affecting other quality requirements of apples, such as hardness, sweetness, sourness, and the like, sometimes rather bringing about improvements in these properties.

Factors participating in production of anthocyanins, red pigments in apple rind, include light, sugar, and temperature, with light being the most important. Irradiation of light (ultraviolet light) onto fruit induces production of anthocyanins. While the mechanism of light-induced production of anthocyanins has not yet been made clear and while not desiring to be bound, the improvement in pigmentation by 5-ALA or a derivative thereof is assumed to arise if 5-ALA or a derivative thereof is related to photosensitization or transmission of the information that light provides to fruit. This assumption is also supported by the fact that the improvement in pigmentation can be obtained even under dark conditions as demonstrated in Example 6 hereinafter described.

The present inventors previously reported that 5-ALA acts as a plant growth accelerator as disclosed in U.S. patent application Ser. No. 07/881,705 (corresponding to EP-A1-0514776). However, unlike phytohormones which have maturation accelerating activity as well as pigmentation accelerating activity, such as auxin, ethylene, and abscisic acid, 5-ALA applied to apples does not exhibit maturation accelerating activity as shown in the Examples hereinafter described. Maturation acceleration causes a softening of the fruit and reduces preservability of fruits and is therefore an unfavorable action for a pigmentation improving agent. In addition, the pigmentation accelerating effect of 5-ALA is exerted even on harvested apples as described in Example 6 below, the mechanism of action of 5-ALA in exercising the pigmentation improving effect seems to be entirely different from that of a growth accelerating effect.

The present invention will now be illustrated in greater detail with reference to Examples, but the present invention should not be construed as being limited thereto. All percents are by weight unless otherwise indicated.

EXAMPLE 1

2 l of an aqueous solution containing 100 ppm of 5-ALA and 0.1% of a commercially available spreading agent "Approach BI" (produced by Kao Corp.) was sprayed onto one of the main branches of a fruit-bearing 20-year-old apple tree (kind: Starking Delicious) with the fruit thereof still having a green color. Onto another main branch of the tree was sprayed 2 l of an aqueous solution containing only Appoach BI in the same concentration as used above (control). The degree of pigmentation of the rind of the fruit was observed 15 days later and 46 days later and rated according to the following standard. The results obtained are shown in Table 1 below. It can be seen that the 5-ALA treatment obviously improved pigmentation and increased the degree of pigmentation.

TABLE 1

| Rating Standard: | |
|---|---|
| 1 | No pigmentation observed at all. |
| 3 | About half the total surface area of the fruits showed pigmentation. |
| 5 | The entire surface of all the fruits showed pigmentation. |

| Group | 15 Days Later | 46 Days Later |
|---|---|---|
| 5-ALA-Treated Group | 3 | 5 |
| Control (non-treated) | 1 | 3 |

EXAMPLE 2

An aqueous solution containing 0 ppm, 100 ppm or 200 ppm of 5-ALA and 0.1% of Approach BI was sprayed onto one of the main branches of a fruit-bearing 25-year-old apple tree (kind: Fuji) with the fruit thereof still having a green color in an amount of 2 l per branch. Fifty four days later, apples were harvested, and the hardness, sweetness, sourness, and degree of pigmentation of the apples were examined. Measurements of the degree of pigmentation were made with a colorimeter "CR-200" (produced by MINOLTA CAMERA CO., LTD.). The results obtained are shown in Table 2 below. In Table 2, L, a, and b values each represent brightness, red and yellow, respectively. The higher the a value, the deeper the red color. It can be seen from the results in Table 2 that the treatment with 5-ALA improved red pigmentation of the apple rind without adversely influencing the quality of the fruit.

TABLE 2

| Group | Hardness | Sweetness | Sourness | L | a | b | $\Delta E(a)$ |
|---|---|---|---|---|---|---|---|
| 5-ALA 100 ppm | 13.5 | 13.4 | 4.70 | 42.36 | 26.00 | 14.61 | 0.88 |
| 5-ALA 200 ppm | 13.5 | 13.4 | 4.45 | 42.45 | 30.93 | 14.90 | 5.81 |
| Control (5-ALA 0 ppm) | 13.0 | 13.4 | 4.55 | 42.01 | 25.12 | 14.72 | — |

EXAMPLE 3

An aqueous solution containing 0 ppm or 300 ppm of 5-ALA and 0.1% of Approach BI was sprayed onto fruit-bearing 12-year-old apple trees (kind: Tsugaru) with their fruit still having a green color in an amount of 4 l per tree (corresponding to 350 l/1000 m$^2$). The number of fruit per tree was about 100.

The apples were harvested 37 days later and evaluated in the same manner as in Example 2. Measurements were made at the equatorial portion of the apples where pigmentation proceeded to the greatest extent. The results obtained are shown in Table 3 below. As is apparent from the results, treatment with 5-ALA brought about marked improvements in fruit quality.

TABLE 3

| Group | L | a | b | Sweetness | Hardness | Sourness |
|---|---|---|---|---|---|---|
| 5-ALA (300 ppm) | 43.31 | 30.72 | 18.60 | 12.0 | 11.5 | 0.24 |
| Control (0 ppm) | 56.28 | 14.31 | 25.89 | 11.2 | 11.7 | 0.26 |

EXAMPLE 4

An aqueous solution containing 0 ppm or 300 ppm of 5-ALA and 0.02% of a commercially available spreading agent "Aiyar" (produced by Agro-Kanesho K. K.) was sprayed on fruit-bearing 25-year-old apple trees (kind: Starking Delicious) with their fruit still having a green color in an amount of 4 l per big branch (corresponding to 350 l/1000 $m^2$). The number of fruit per big branch was about 100.

The apples were harvested 42 days later and evaluated in the same manner as in Example 2. The results obtained are shown in Table 4 below. It can be seen that the treatment with 5-ALA improved the red pigmentation of the rind.

TABLE 4

| Group | L | a | b | Sweetness | Hardness | Sourness |
|---|---|---|---|---|---|---|
| 5-ALA (300 ppm) | 38.44 | 36.78 | 17.89 | 13.3 | 13.6 | 0.31 |
| Control (0 ppm) | 40.02 | 32.37 | 18.02 | 13.4 | 13.7 | 0.29 |

EXAMPLE 5

An aqueous solution containing 0 ppm or 300 ppm of 5-ALA and 0.1% of Approach BI was sprayed onto fruit-bearing 25-year-old apple trees (kind: Fuji) in an amount of 4 l per big branch (corresponding to 350 l/1000 $m^2$). The number of fruit per big branch was about 100.

The apples were harvested 53 days later and evaluated in the same manner as in Example 2. The results obtained are shown in Table 5 below. As is apparent from the results in Table 5, the treatment with 5-ALA improved the red pigmentation of the apple rind, reduced sourness, and enhanced sweetness. In other words, the agent according to the present invention brought about marked improvements in quality of apples.

TABLE 5

| Group | L | a | b | Sweetness | Hardness | Sourness |
|---|---|---|---|---|---|---|
| 5-ALA (300 ppm) | 44.45 | 38.77 | 12.85 | 15.1 | 15.8 | 0.35 |
| Control (0 ppm) | 45.82 | 31.50 | 15.33 | 14.8 | 15.8 | 0.37 |

EXAMPLE 6

Out of commercially available apples of various kinds, those with insufficient pigmentation were purchased. The uniformly colored portion of each apple was marked with a felt-tipped oily ink pen, and the marked portion was divided into 4 test areas. One half of the marked portion, composed of two test areas, was coated with an aqueous solution containing 250 ppm of 5-ALA and 0.1% of a commercially available spreading agent "Neosuterin" (produced by Kumiai Chemical Industry Co., Ltd.) with a brush, while the other half (the other two test areas) was coated with an aqueous solution of the same composition but without any 5-ALA. After drying the solution in air, the test areas were exposed to light of a halogen lamp (10000 lux) for 48 hours with half of each coated area (half the marked portion) being covered with aluminum foil for light shielding, and the degree of pigmentation of each test area was measured using a CR-200. The results obtained are shown in Table 6 below. The results in Table 6 demonstrate that the degree of pigmentation can be improved even by post-harvest application of the method for improving pigmentation of apple rind according to the present invention and that the pigmentation improving effect can be achieved even under dark conditions.

TABLE 6

| Kind of Apple | Lab Value | Irradiated Area | | Non-Irradiated Area | |
|---|---|---|---|---|---|
| | | Control | 5-ALA 250 ppm | Control | 5-ALA 250 ppm |
| Tsugaru-1 | L | 98.79 | 54.75 | 72.42 | 69.57 |
| | a | 34.55 | 43.97 | 23.75 | 36.33 |
| | b | 48.71 | 67.41 | 74.85 | 62.26 |
| Tsugaru-2 | L | 79.88 | 76.23 | 81.65 | 78.00 |
| | a | 3.30 | 9.26 | 5.60 | 11.01 |
| | b | 98.97 | 82.99 | 88.46 | 80.33 |
| Jonagold | L | 57.72 | 47.85 | 56.64 | 55.62 |
| | a | 54.87 | 60.17 | 49.81 | 51.37 |
| | b | 92.79 | 75.03 | 87.06 | 81.45 |
| Starking | L | 45.53 | 54.13 | 74.32 | 74.58 |
| | a | 55.57 | 57.46 | 41.86 | 43.67 |
| | b | 71.45 | 42.07 | 53.80 | 55.87 |
| Santsugaru | L | 67.47 | 65.20 | 94.01 | 83.04 |
| | a | 30.11 | 31.42 | 5.69 | 7.73 |
| | b | 77.39 | 76.51 | 77.56 | 70.92 |
| Sensyu | L | 60.06 | 53.55 | 65.85 | 54.56 |
| | a | 47.68 | 55.14 | 35.62 | 54.06 |
| | b | 82.92 | 66.40 | 80.20 | 70.56 |
| Jonathan | L | 54.49 | 59.05 | 85.85 | 83.89 |
| | a | 53.66 | 55.56 | 7.19 | 24.40 |
| | b | 74.11 | 64.39 | 90.05 | 89.77 |

The present invention makes it possible to accelerate red pigmentation of apple rind and to improve the degree of pigmentation without adversely influencing the human body, the environment and quality of apples.

While the invention has been described in detail and with reference to specific examples thereof, it will be apparent to one skilled in the art that various changes and modifications can be made therein without departing from the spirit and scope thereof.

What is claimed is:

1. A method for improving the pigmentation of the rind of anthocyanin-containing apples comprising treating fruit-bearing apple trees or apples before or after harvesting with an effective amount of an agent for improving pigmentation of the rind of apples comprising 5-aminolevulinic acid, a salt thereof or a mixture thereof as an active component.

2. A method as claimed in claim 1, wherein said apples are Delicious, Starking Delicious, Akane, Fuji, Tsugaru, Mutsu, Kokko, Jonathan, Hokuto, Shin-sekai, Hakkunain, Jonagold, Redgold, Sensyu, McIntosh, Sansa, Rome Beauty, Winesap or Gala.

3. A method as claimed in claim 1, wherein 5-aminolevulinic acid, a salt thereof or a mixture thereof is present in a concentration of from 1 to 1000 ppm.

4. A method as claimed in claim 1, wherein 5-aminolevulinic acid, a salt thereof or a mixture thereof is present in a concentration of from 3 to 800 ppm.

* * * * *